United States Patent
Savard et al.

(10) Patent No.: US 8,862,222 B2
(45) Date of Patent: Oct. 14, 2014

(54) NON-INVASIVE MEASURING OF LOAD-INDUCED ELECTRIC POTENTIALS IN DIARTHROIDIAL JOINTS

(75) Inventors: Pierre Savard, Sainte Thérèse (CA); Michael Buschmann, Montreal (CA); John Hardin, New York, NY (US)

(73) Assignee: Polyvalor, Limited Partnership, Montreal, Quebec (CA)

( * ) Notice: Subject to any disclaimer, the term of this patent is extended or adjusted under 35 U.S.C. 154(b) by 799 days.

(21) Appl. No.: 12/920,242

(22) PCT Filed: Mar. 2, 2009

(86) PCT No.: PCT/CA2009/000249
§ 371 (c)(1),
(2), (4) Date: Oct. 20, 2010

(87) PCT Pub. No.: WO2009/105895
PCT Pub. Date: Sep. 3, 2009

(65) Prior Publication Data
US 2011/0034797 A1    Feb. 10, 2011

Related U.S. Application Data

(60) Provisional application No. 61/064,368, filed on Feb. 29, 2008.

(51) Int. Cl.
| A61B 5/05 | (2006.01) |
| A61B 5/04 | (2006.01) |
| A61B 5/103 | (2006.01) |
| A61B 5/117 | (2006.01) |
| A61B 5/00 | (2006.01) |
| A61N 1/04 | (2006.01) |

(52) U.S. Cl.
CPC ............... *A61B 5/04* (2013.01); *A61B 5/4528* (2013.01); *A61B 5/4514* (2013.01); *A61B 5/6828* (2013.01); *A61B 5/05* (2013.01); *A61N 1/0476* (2013.01)

USPC .......... 600/547; 600/382; 600/384; 600/587; 600/595

(58) Field of Classification Search
USPC ......... 600/546–547, 382, 384, 552, 553, 587, 600/595
See application file for complete search history.

(56) References Cited

U.S. PATENT DOCUMENTS 5,513,651 A * 5/1996 Cusimano et al. ............ 600/595
5,779,651 A * 7/1998 Buschmann et al. ......... 600/587

(Continued)

FOREIGN PATENT DOCUMENTS

EP    1227756    10/2000
EP    0961575     1/2004

OTHER PUBLICATIONS

Schmidt-Rohlfing et al. "Mechanically induced electrical potentials of articular cartilage". Journal of Biomechanics, vol. 35, Issue 4, Apr. 2002, pp. 475-482.*

(Continued)

*Primary Examiner* — Devin Henson
(74) *Attorney, Agent, or Firm* — Norton Rose Fulbright Canada LLP

(57) ABSTRACT

There is described a method for non-invasively measuring electrical activity in a joint of a subject, the method comprising: removably attaching in a non-invasive manner at least two electrodes to a skin surface around an articulation comprising the joint; generating electroarthrographic potentials within the joint by loading the articulation; capturing the electroarthrographic potentials using the at least two electrodes; discriminating between electroarthrographic potentials originating from joint tissue activity and those from other sources; and generating measurement signals representing the electrical activity of joint tissue.

25 Claims, 12 Drawing Sheets

(56) References Cited

U.S. PATENT DOCUMENTS

| | | | |
|---|---|---|---|
| 6,735,468 B2 * | 5/2004 | Treppo et al. | 600/547 |
| 6,882,880 B2 | 4/2005 | Treppo et al. | |
| 2004/0167420 A1 * | 8/2004 | Song et al. | 600/547 |
| 2004/0225211 A1 * | 11/2004 | Gozani et al. | 600/382 |
| 2005/0113691 A1 * | 5/2005 | Liebschner | 600/437 |

OTHER PUBLICATIONS

International Search Report PCT/CA2009/000249.

Garon et al., "Streaming potentials maps are spatially resolved indicators of amplitude, frequency and ionic strength dependant response of articular cartilage to load", Journal of Biomechanics, vol. 35, No. 2, Feb. 2002.

* cited by examiner

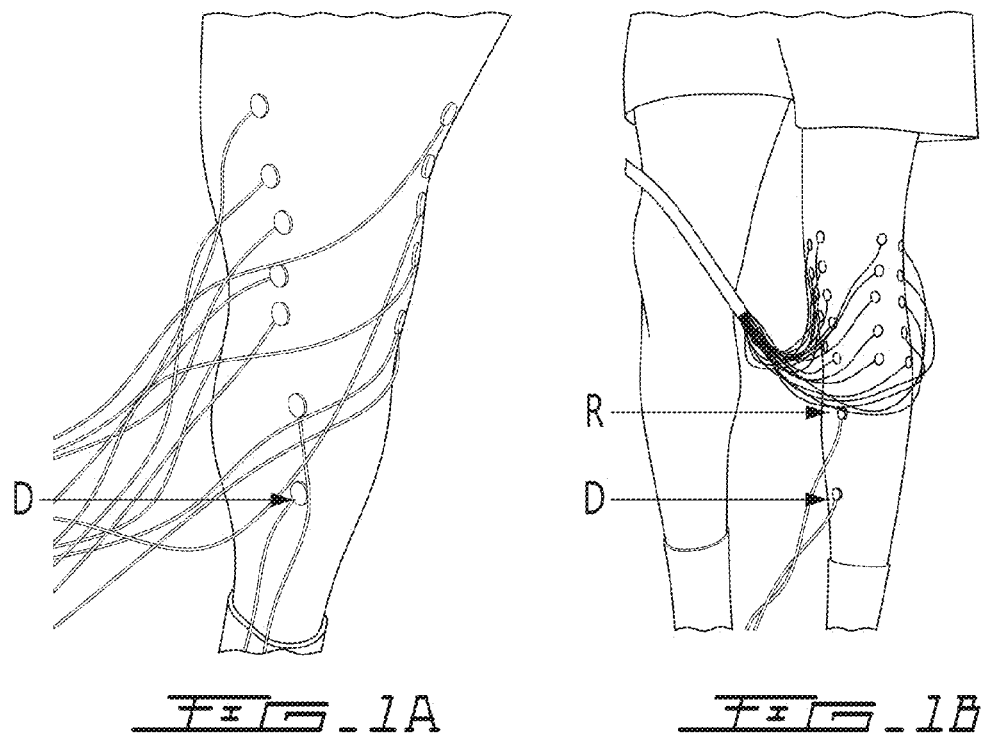
FIG_1A   FIG_1B
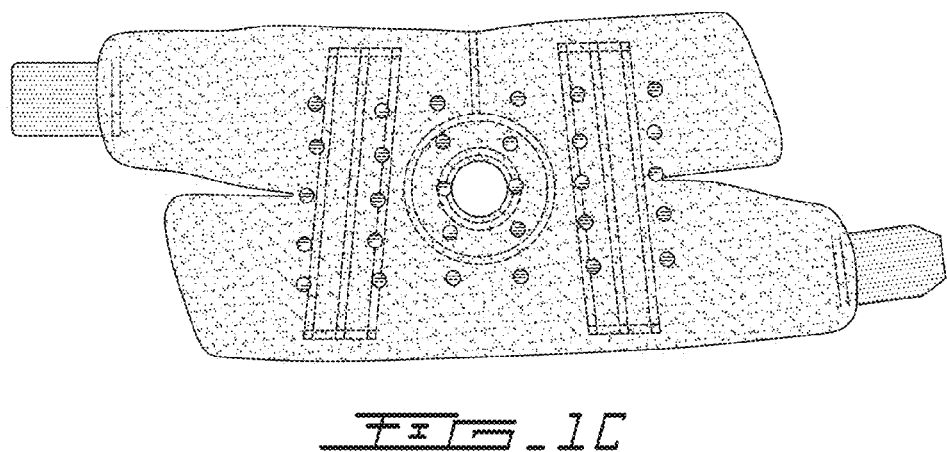
FIG_1C

FIG_3

FIG_4

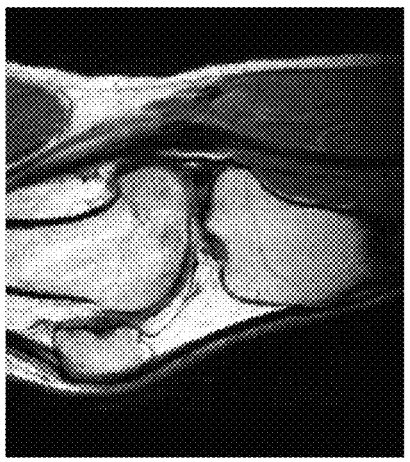
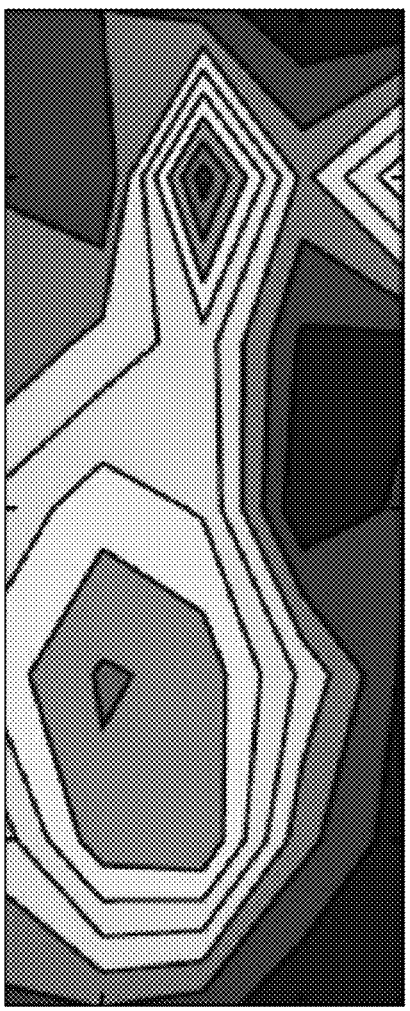
FIG. 5

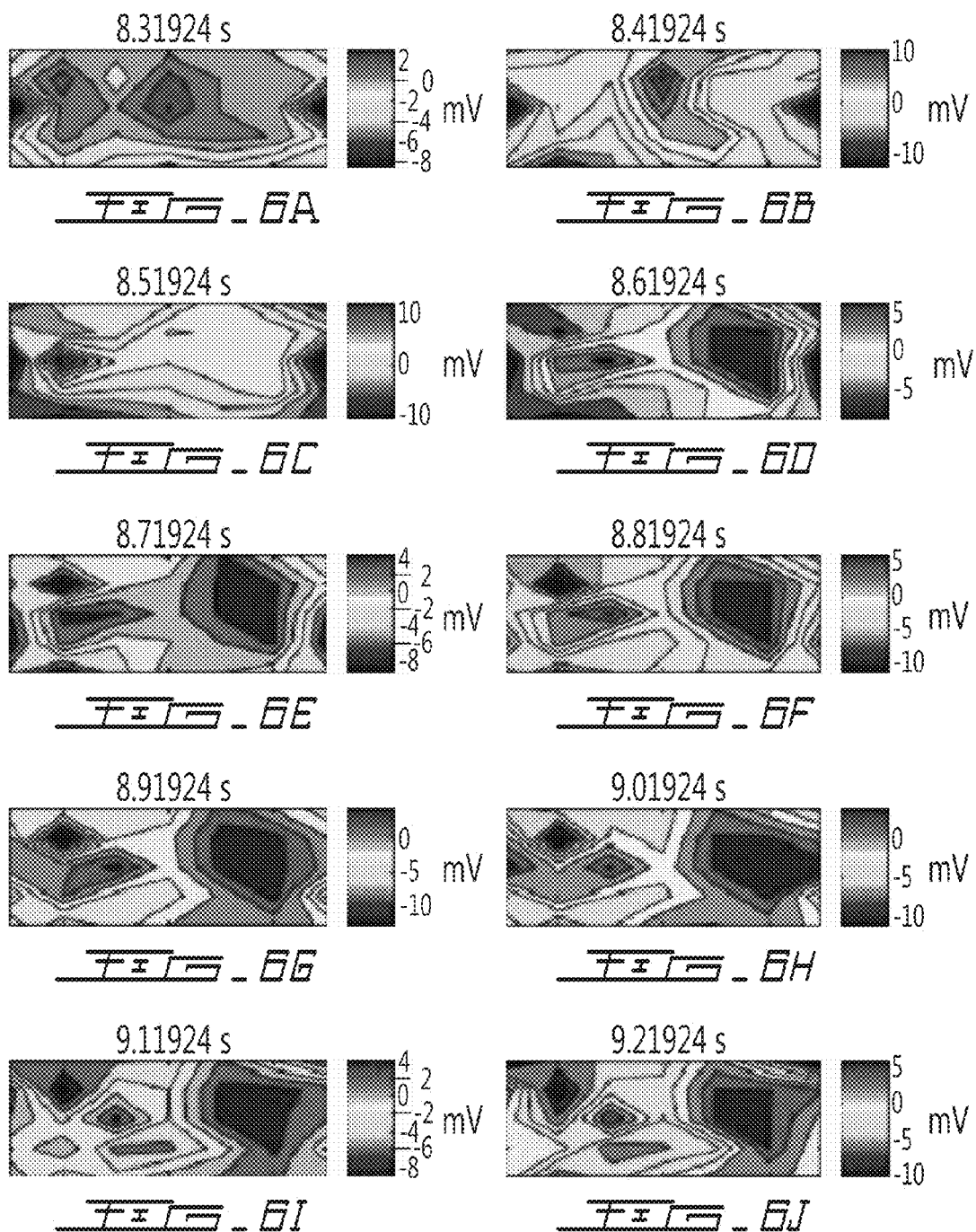

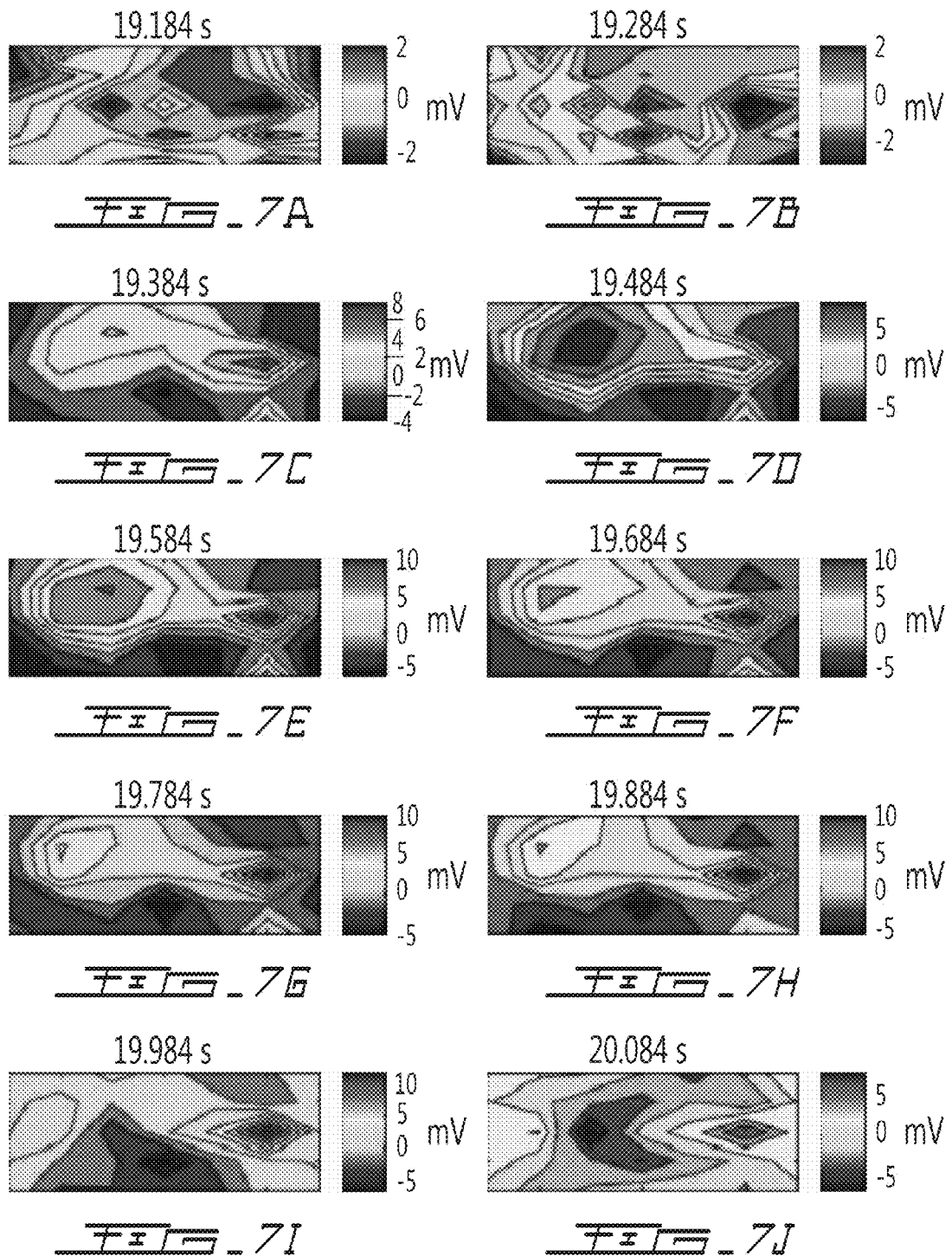

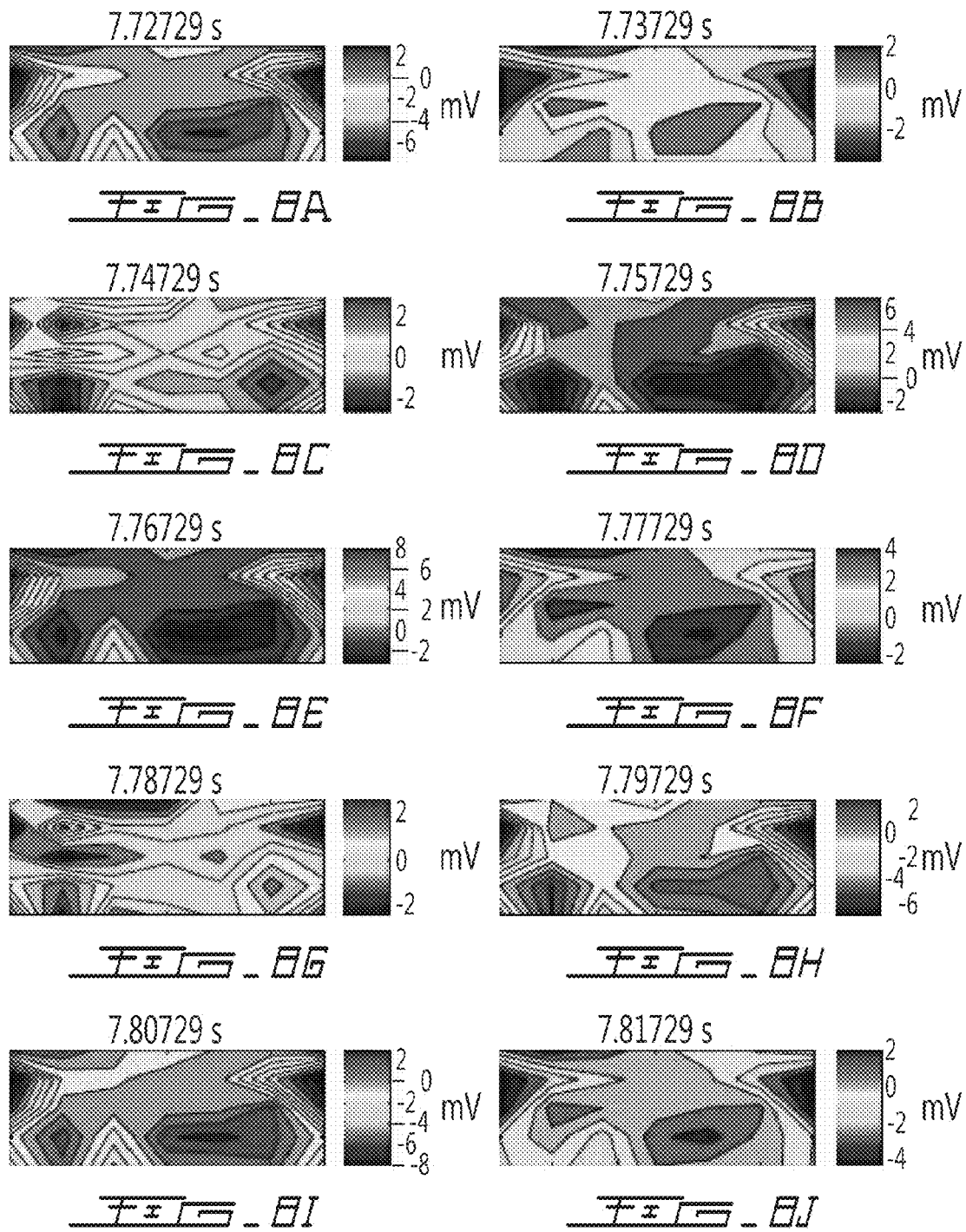

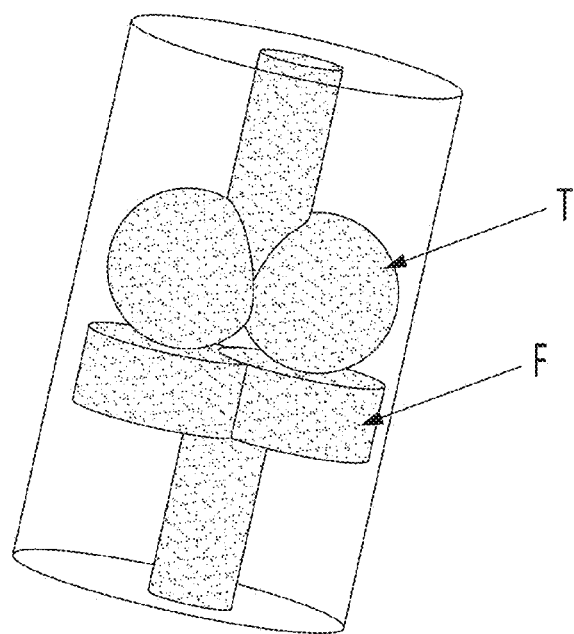
_FIG_ 9A
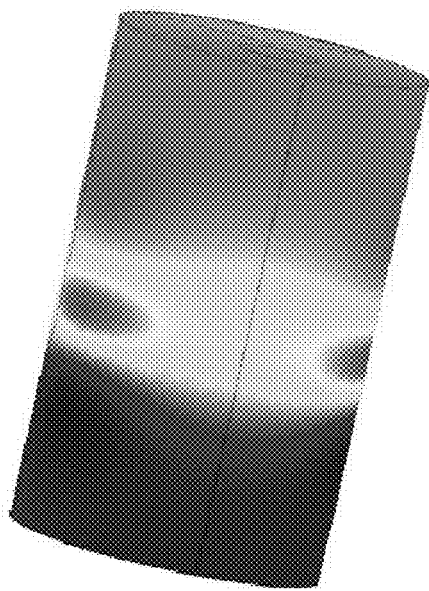 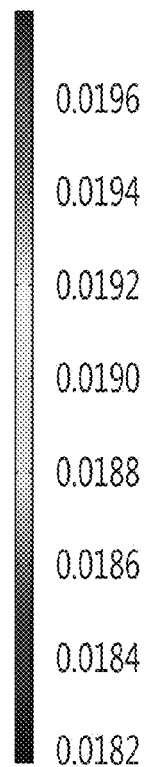
_FIG_ 9B

NON-INVASIVE MEASURING OF LOAD-INDUCED ELECTRIC POTENTIALS IN DIARTHROIDIAL JOINTS

CROSS-REFERENCE TO RELATED APPLICATIONS

This application claims priority under 35 U.S.C. §119(e) from U.S. Provisional Patent Application No. 61/064,368, flied on Feb. 29, 2008.

TECHNICAL FIELD

The present description relates to a method for non-invasively measuring load-induced electroarthrographic potentials in diarthroidial joints.

BACKGROUND

Diarthroidial joints such as the knee permit mobility and movement in people and animals via a complex structure containing interacting and interdependent elements such as articular cartilage, bone, ligaments, tendons, synovium, the joint capsule, vasculature, nerves and other soft tissues. The joint is considered to be an organ that fulfils this function of permitting movement and mobility when healthy, but can be subject to disease and degeneration of its various structures mentioned above. Joint disease is often referred to as arthritis and there are two major forms of arthritis, osteoarthritis and rheumatoid arthritis, the latter bearing a more inflammatory aspect than the former, while the former is much more prevalent, affecting up to 15% of the population in developed countries.

Although the etiology and pathogenesis of the various forms of arthritis are not entirely understood, most of these disease states lead to a painful joint that has significant damage to articular cartilage, often with areas of articular cartilage that are entirely denuded down to subchondral bone. Since articular cartilage provides the smooth nearly frictionless surface that permits joint loading and protects subchondral bone from direct articulation, degeneration of articular cartilage is considered a hallmark and common endpoint of joint disease that requires treatment, often in the form of prosthetic joint replacement.

Current methodologies that are applied by clinicians to assess joint function and disease include physical examination and imaging technologies such as magnetic resonance imaging or computed tomography.

Although these techniques provide a wealth of information, none have been able to provide sensitive and specific diagnostic information early enough in the disease process to permit successful interventions and development of therapeutics that are effective prior to end-stage disease.

It would thus be highly desirable to be provided with a method for diagnosis degeneration of articular cartilage and joint disease at stages that are treatable, prior to necessitating joint replacement.

SUMMARY OF THE DESCRIPTION

The system and method described herein allow non-invasive measurement of electrical activity of joints and articulations.

In accordance with a first broad aspect, there is provided a method for non-invasively measuring electrical activity in a joint of a subject, the method comprising: removably attaching in a non-invasive manner at least two electrodes to a skin surface around an articulation comprising the joint; generating electroarthrographic potentials within the joint by loading the articulation; capturing the electroarthrographic potentials using the at least two electrodes; discriminating between electroarthrographic potentials originating from joint tissue activity and those from other sources; and generating measurement signals representing the electrical activity of joint tissue.

In accordance with a second broad aspect, there is also provided a system for non-invasively measuring an electrical activity in a joint of a subject, the system comprising: at least two spaced apart electrodes for contacting the skin around an articulation comprising the joint and capturing electroarthrographic potentials generated within the joint by loading the articulation; a processing device adapted to receive the electroarthrogaphic potentials from the at least two electrodes and to discriminate between electroarthrographic potentials originating from joint tissue activity and those from other sources; and a signal generating module adapted to receive the electroarthrographic potentials originating from joint tissue activity and generate measurement signals representing the joint tissue activity.

In accordance with a third broad aspect, there is provided the use of the method for non-invasively measuring an electrical activity in a joint as disclosed herein or the system as disclosed herein for determining function of joint tissues, degradation of joint tissues, injury of joint tissues, osteoarthritis or arthritis in a patient.

In one embodiment, the signals generated are displayed as an electroarthrogram. In some embodiments, goniometers, accelerometers or sensors are placed near the joint to measure the angle of the joint and/or forces exerted by the subject during loading prior to generating electroarthrographic potentials within the joint by loading the articulation.

In one embodiment, the step of discriminating between electroarthrographic potentials originating from joint tissues and those from other sources further comprises subtracting at each time instant a weighted average of the electrical potentials originating from the electrodes so as to measure the electroarthrographic potentials with respect to an absolute reference.

In some embodiments, the step of discriminating between electroarthrographic potentials originating from the loading of the articulation and those from other sources comprises band pass filtering, such as by using a low pass filter or a high pass filter.

In some embodiment, the method described herein further comprises the step of calculating electrical sources within the joint and representing the electrical sources as electric fields, currents, polarization or charges.

The signals generated can be displayed as disclosed herein as sequences, movies, isopotential maps or 3D potential surfaces.

The electrodes can be attached using a non-toxic adhesive, or provided on a fabric, such as a sock, belt, cuff, sleeve, or any other type of apparel that can be worn on the body at the appropriate location. The electrodes can be integrated inside the apparel or provided directly on the skin surface.

In some embodiments, loading of the joints as disclosed herein can be done by electromechanical means, piezoelectric means or manual means.

The electrodes disclosed herein can be selected from the group consisting of electroencephalographic electrodes, self-adhesive electrocardiographic electrodes and electrodes embedded in a cuff or a sleeve adapted to fit around the joint. In one embodiment, the electrodes can be made of Ag—AgCl.

In one embodiment, the electrodes can be evenly placed in contact with the skin around the joint, the electrodes being a reference electrode and a drive electrode to inject current so as to maintain an average potential of the subject similar to that of an electrical ground of an amplifier so as to minimize electrical interference.

In this specification, the term "electrode" is intended to mean a device that emits, controls or receives electricity.

BRIEF DESCRIPTION OF THE DRAWINGS

Having thus generally described the nature of the present disclosure, reference will now be made to the accompanying drawings, showing by way of illustration, at least one embodiment thereof, and in which:

FIGS. 1a, 1b and 1c illustrate different embodiments for the surface electrode arrays such as (a) pasted electroencephalographic electrodes, (b) self-adhesive electrocardiographic electrodes, and (c) a cuff with embedded electrodes and Velcro® fasteners for rapid positioning;

FIG. 5 illustrates the format of the isopotential maps that are computed from processed data as shown in FIGS. 3 and 4, wherein these isopotential maps are used to analyze and interpret the knee surface potentials in relationship with the anatomy of the knee indicated by the medial to back positioning, lighter colors area corresponding to positive potentials and dark colors area to negative potentials, in accordance with an embodiment;

FIGS. 6A-J illustrates a sequence of isopotential maps computed from the data of FIG. 3, recorded over the surface of the left knee every 100 ms as the subject starts to stand on his left leg, wherein the maps show the spatial-temporal evolution of the potentials that can be used to locate the internal electrical sources at the level of the articular surfaces of the medial and lateral compartments of the knee, in accordance with an embodiment;

FIGS. 7A-J illustrate a similar sequence of isopotential maps as those of FIGS. 6A-J, recorded on a different subject, wherein two potential maxima are observed at the mid level over the lateral and medial compartments, but the lateral maximum is greater in amplitude compared to that of the subject shown in FIG. 6, in accordance with an embodiment;

FIGS. 8A-J illustrates a sequence of isopotential maps computed from the data in FIG. 4 as the subject stands on a vibrating platform with a frequency of 12 Hz, wherein two potential extrema are observed at the mid level over the lateral and medial compartments, their polarity inverses after half a cycle and the pattern repeats itself after one full cycle, in accordance with an embodiment;

FIG. 9A illustrates a simplified computer model of the knee with regions of different electrical conductivities such as the tibia (T) and femur (F), and the potential distribution that is generated on the surface of this model, in accordance with an embodiment;

FIG. 9B illustrates the computer model of FIG. 9A by an impressed current density located at the periphery of the two regions of compressed cartilage, wherein two potential extrema are observed at the mid level over the lateral and medial compartments, these two extrema are similar to the extrema observed on the measured potential distributions shown in FIGS. 6, 7 and 8, in accordance with an embodiment;

DETAILED DESCRIPTION

There is described herein a method of measuring load-induced electric fields originating from articular cartilage in an intact joint, non-invasively. These measurements may then be used as a means of assessing the health of articular cartilage and other joint tissues, and thus the presence and type of arthritis, since these streaming potentials accurately reflect the structure and function of articular cartilage and other joint tissues. The non-invasive aspect of the method described herein allows the use of an easily implemented tool for assessing and following joint health in patients in a clinical setting.

Figure 11:
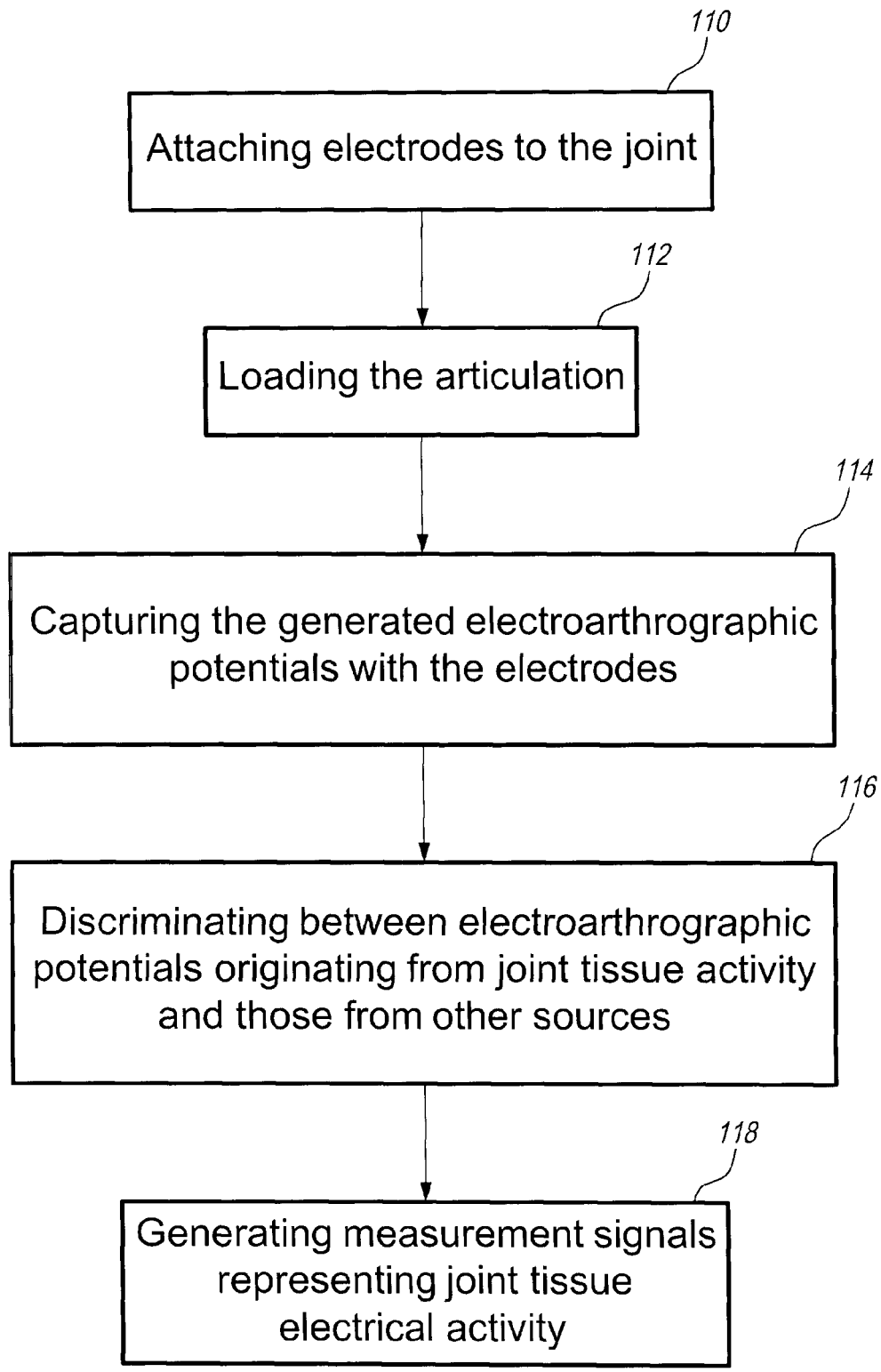
FIG. 11 is a flow chart illustrating an embodiment of the method for non-invasively measuring electrical activity in a joint of a subject.

Reference is made to FIG. 11, which illustrate one embodiment of the method. The electrodes are first attached to the joint 110. This may be done directly or indirectly. The articulation is loaded 112 in order to generate the electrical activity within the cartilage. Generated electroarthrographic potentials are captured by the electrodes 114. The captured signals are processed by discriminating between the electroarthrographic potentials that originate from the joint tissues, and those from other sources of electric activity 116. Measurement signals are then generated using the electroarthrographic potentials that originate from joint tissues 118.

There have been no previous reports of non-invasive detection of load-induced electrical activity in an intact diarthroidial joint. This may be due to an assumed complexity of the measurement and difficulty in distinguishing electrical activity from cartilage versus other sources as well as an assumed low amplitude of electrical potentials at the skin surface that are produced by streaming potentials in cartilage and other joint tissues. More specifically, it is a common belief that electrical activity from cartilage is too small to be detected at the surface of the knee, and their distribution too complex to analyze effectively, since the assumed small signals needs to pass through various tissues and muscles surrounding the cartilage.

When using known apparatuses such as the Arthro-BST™ (described in U.S. Pat. No. 5,779,651), such measurements are accomplished ex vivo or invasively, for example through arthroscopic portals to insert the electrodes, access and directly compress the articular surface of the cartilage with the electrodes, thereby removing the assumed problem of small signals and complexity of signals after passing through other tissues to the skin. Such direct invasive compressions load the cartilage, generating electric potentials in the order of a few mV. The inserted microelectrodes detect load-induced electric potentials, called streaming potentials, in the cartilage. Tissue loading induces interstitial fluid flow that displaces excess sodium relative to the negative charge on the proteoglycan, thus producing charge displacement and electric fields in the tissue. These streaming potentials are very sensitive to cartilage degeneration since loss of proteoglycan and breakdown of collagen are both early events in cartilage degradation and arthritis and both of these events will reduce the amplitude of load induced electric fields. The loading of the cartilage by directly compressing the surface with an electrode only produces electric potentials which are small in amplitude and is a necessarily invasive procedure.

In the method described herein, multiple electrodes are placed in contact with the skin around the knee joint and electrical activity is measured non-invasively while the knee is loaded by, for example but not restricted to, balancing movements or with a vibration platform.

The loading of the cartilage described herein using body weight can allow a greater compression of the cartilage compared to simply compressing the surface of cartilage with an electrode, increasing greatly the amplitude of the electric potentials which are generated and the volume of tissue from which signals are generated. Loading the knee and the cartilage by, for example, balancing movements or with a vibration platform generates electric potentials that are detectable at the surface of the knee. These potentials are in the order of 10-20 mV for example, which is similar to those generated when loading the cartilage by simple compression of its surface with an electrode.

Electric potentials with the same periodicity and form as the loading signal confirm their origin from joint tissues rather than due to muscular activity. When the surface map of electric activity around the knee is analyzed visually and mathematically to identify its source within the knee, dipolar sources are located at the articular surface and are aligned in a direction consistent with interstitial fluid flow (see FIGS. 10A and B) convecting excess sodium out of the articular cartilage and leaving net negative charge inside. A dipolar source can be identified in each compartment of the knee, one in the medial compartment and one in the lateral compartment, with magnitudes and orientations that vary between individuals.

Thus it is disclosed a method to obtain and analyze load-induced electric fields in joints, non-invasively, for the purpose of assessing joint function and diagnosing disease in people and animals.

The compression of the cartilage and other joint tissues including meniscus, ligaments and subchondral bone generates electric fields that produce the streaming potentials. These electric fields are produced in vivo in an intact joint that is loaded and these electric fields and potentials from the loaded articular cartilage and other joint tissues also produce electrical potentials on the surface of the body that can be non-invasively measured with an appropriate recording system and signal processing. These surface potentials measured around a loaded joint are identified as electroarthrographic potentials.

The data in FIGS. 2 to 8 are examples of electroarthrograms (EAG) and the entire process of recording and displaying electroarthrographic potentials for functional or diagnostic purposes, known as electroarthrography.

A recording system for the measurement of electroarthrographic potentials uses at least two electrodes. In some embodiments, a large number of surface electrodes are distributed evenly on the body surface, around the articulation, as shown in FIG. 1. Any number of surface electrodes, such as 2, 3, 4, 5, 6, 7, 8, 9, 10, 11, 12, 13, 14, 15, 16, 17, 18, 19, 20, and more than 20 electrodes forming electrode arrays are used for electrical potential reference. The recording systems measure the potential difference between the electrode of interest (or drive electrode; D in FIG. 1) and a reference electrode (R in FIG. 1), while the potential of the reference electrode does not usually correspond to the true zero potential, which may complicate the analysis of the measured potentials. However, since the integral over a closed surface of potentials generated by biological electrical sources is equal to zero (no net charge generation), a new potential reference can be computed by averaging the potentials recorded with uniformly distributed electrodes at a given instant. This new potential reference can be considered the true zero potential since it corresponds to the average potential of the electrodes in the unloaded condition. This new potential reference is then subtracted from the potential measured at each electrode to generate new surface potentials relative to the new reference potential.

Spatial discrimination of the electroarthrographic sources is generated. Measured potentials can originate from compressed cartilage and other joint tissues, but also from other sources such as electrode movement artifacts and electromyographic sources. However, current sources inside a volume conductor generate potentials on the surface of the volume conductor that have spatial patterns that are specific to the location of the electrical sources and can be used to discriminate between deep sources located at the articular surface versus sources produced by other undesired sources.

If the signal from one electrode is intermittent because of poor skin contact, this signal can be interpolated using signals from neighboring electrodes.

Different types of low noise, low impedance electrodes can be used, as shown in FIG. 1, such as pasted electroencephalographic electrodes (A), self-adhesive electrocardiographic electrodes (B), and electrodes embedded in a cuff with Velcro® fasteners for rapid positioning (C). The signals are amplified, sampled and converted to a digital format for computer processing.

Figure 2:
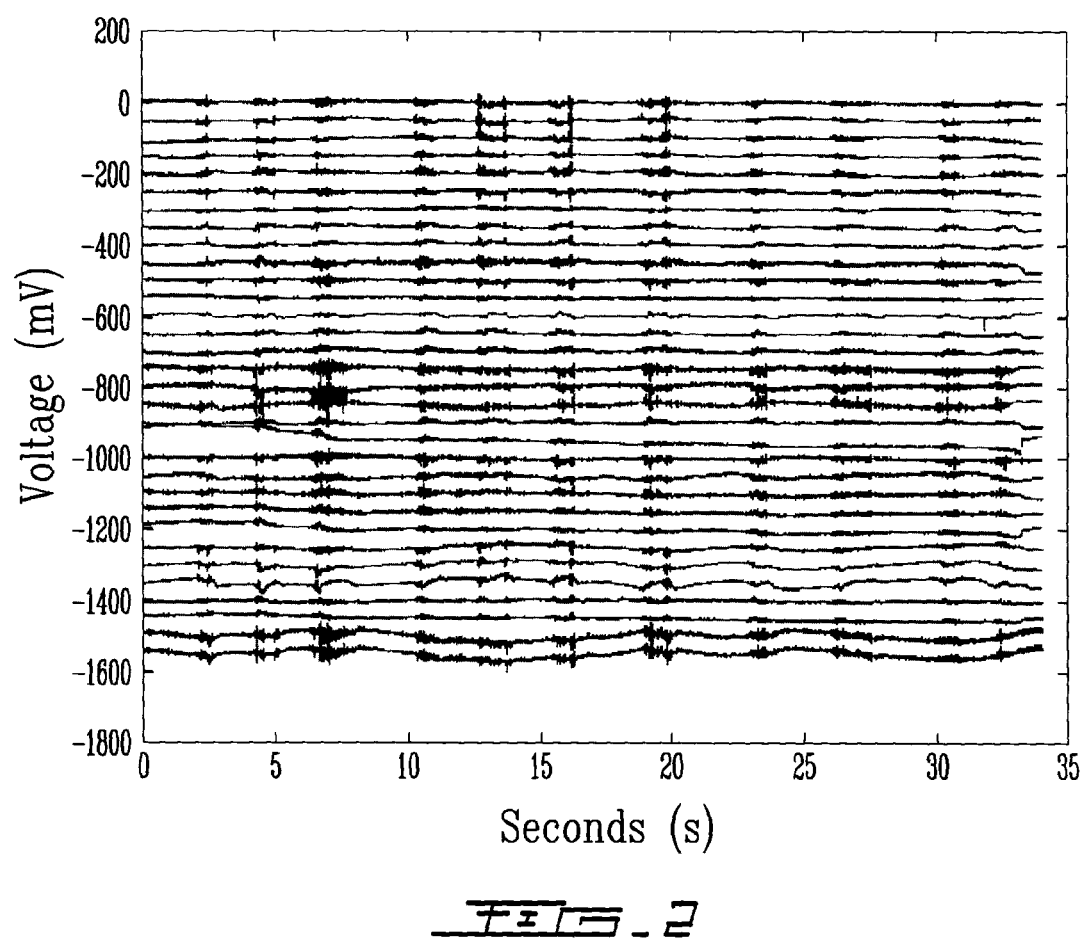
FIG. 2 illustrates unfiltered potentials measured over the surface of the knee wherein the subject alternatively stands on his left leg, then on his right leg with a period of about 2-3 seconds and wherein some of the signals show electromyographic (EMG) interference originating from underlying muscles or baseline drift, the time scale being expressed in seconds, in accordance with an embodiment.
Figure 3:
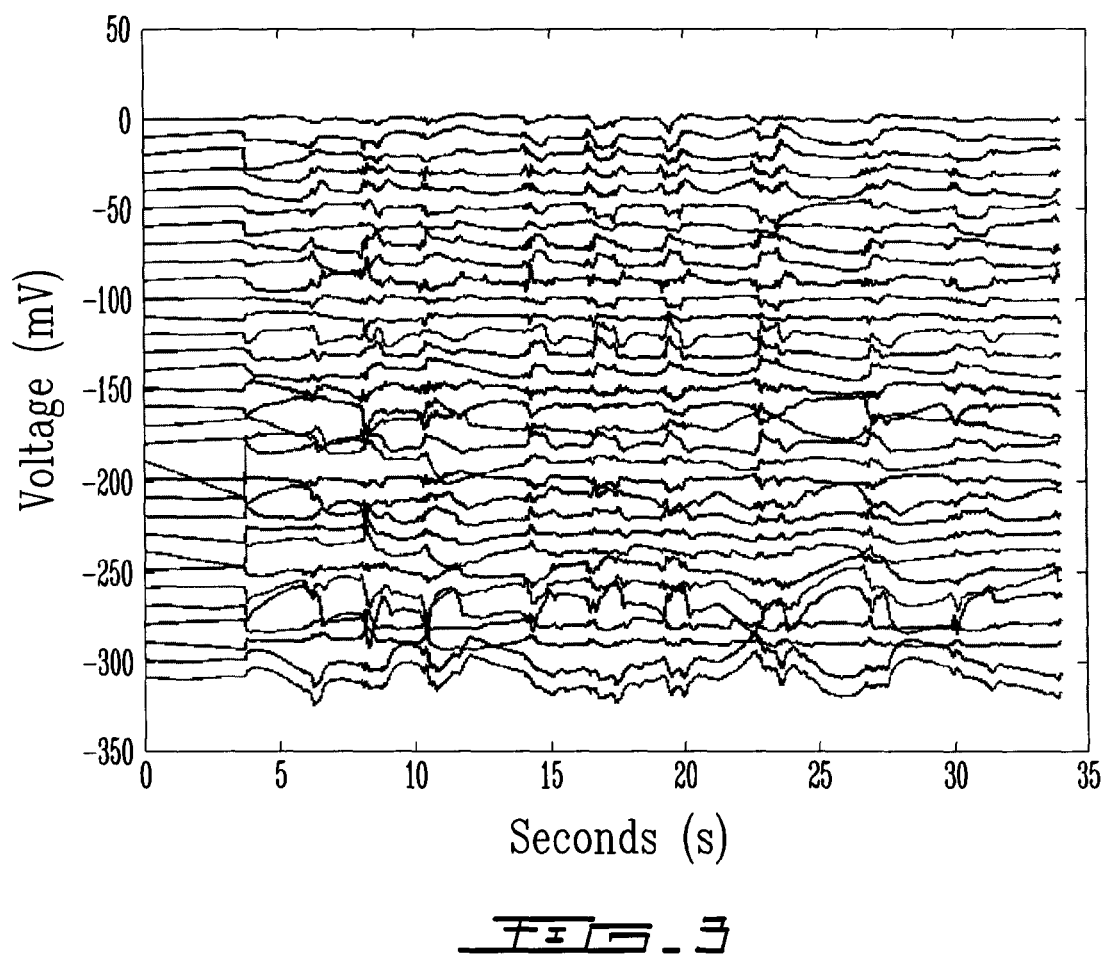
FIG. 3 illustrates the same signals as in FIG. 2, but after signal processing consisting of computing a new potential reference and band-pass filtering (0.1-5.0 Hz) to reduce the EMG interference and the baseline drift, the time scale being expressed in seconds and the maximum amplitude of the filtered signals being 10 to 15 mV, in accordance with an embodiment.
Figure 4:
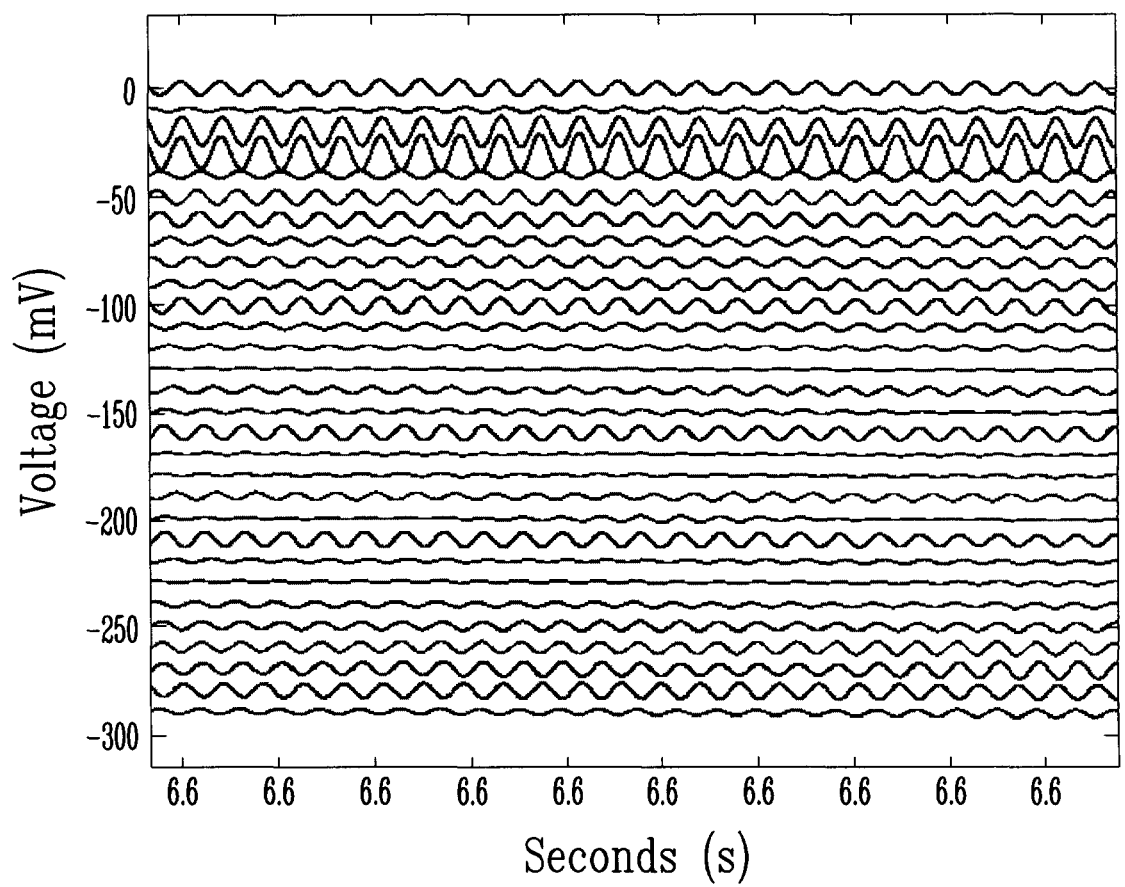
FIG. 4 illustrates band-pass filtered (12 Hz center frequency) signals measured over the knee when the subject stands on a vibrating platform, which is an alternative method to load the articulation, in addition to movements controlled by the subject as illustrated and accomplished in FIGS. 2 and 3, the time scale being expressed in seconds, in accordance with an embodiment.

Signal pre-processing is used to compute the new potential reference, as described above, and also to filter the EAG signals. The objective of this filtering process is to retain the frequency components that correspond to the mechanical loading of the articulation that generates the electroarthrographic potentials, while reducing and eliminating the other frequency components that may be associated with sources of interference. Some of these sources of interference are: the baseline drift due to electrode polarization; the interference from the electrical distribution network (50 Hz or 60 Hz); the EMG interference originating from underlying muscles (FIG. 2). Thus, low pass filtering may be used to reduce the high frequency EMG interference and the interference from the electrical network, whereas high pass filtering may be used to reduce the baseline drift. The cutoff frequencies of the filters depend on the frequency of the mechanical loading of the articulations. For example, a band-pass filter with cutoff points at 0.1 Hz and 5.0 Hz can be used when the subject alternatively stands on his right then on his left leg every 2-3 seconds (FIGS. 3, 6, 7 and 10), whereas a band pass filter with a center frequency of 12 Hz and a bandwidth of 2 Hz is used when the subject stands on a vibrating platform with a vibrating frequency of 12 Hz (FIGS. 4 and 8). The cutoff frequency values and bandwidth values that are given here are examples and other frequencies can be used. Either analog or digital filters can be used for this purpose.

Displaying the spatial and temporal evolution of the preprocessed potentials can be used to estimate the location of the electrical sources within the region of the knee articular surfaces, thus discriminating the electroarthrographic potentials originating from streaming potentials of articular cartilage versus other sources. Different displays can be used such as a sequence of 3D surfaces depicting the time-varying potential distributions. As an example, a sequence of isopotential maps, whose format is shown in FIG. 5, are used. In these maps, isopotential lines join points that have the same potential after preprocessing and a color code or intensity code is associated with the amplitude of the potentials.

FIG. 6 illustrates a sequence of isopotential maps recorded over the surface of the left knee at every 100 ms as the subject stands on his left leg. After 8.519 seconds, a pattern with two maxima along the horizontal center of the maps, one over the medial surface and the other on the lateral surface, starts to emerge. The lateral maximum is initially the strongest but the medial one then becomes greater and decreases. The maximum amplitude is about 10 mV. In reference to FIG. 5, these two potential maxima are consistent with internal electrical sources corresponding to two current dipoles located at the articular surfaces of the knee, i.e. where the medial and lateral condyles articulate with opposing tibial articular cartilage and with meniscus. Such sources are expected for streaming potentials in articular cartilage since compression will force excess counterions (sodium) out of cartilage at the edge of the articulation, leaving a net negative charge inside the cartilage from unbalanced sulfate and carboxyl groups of proteoglycan.

A similar pattern can be observed for a different subject in FIG. 7: two potential maxima are again observed at the mid level over the lateral and medial compartments, but for this subject the lateral maximum is greater than that of the previous subject.

An alternative means to load the knee, namely using a vibrating plate, generates two potential extrema again that are observed at the mid level of the lateral and medial compartments. Here since the signal is periodic, the potential patterns display an inverting polarity halfway through the loading cycle and a repeating pattern after every full cycle (FIG. 8).

As demonstrated hereinabove, a visual analysis of the isopotential maps can be used to estimate the location of the electrical sources within the region of the knee articular surfaces, thus discriminating the electroarthrographic potentials originating from streaming potentials of articular cartilage versus other sources (electrode artifacts, EMG). FIG. 9 confirms the visual analysis and the localization of the bioelectrical sources in regions of compressed cartilage: potential distributions that are computed over the surface of a computer model of the knee show two potential extrema at the mid level over the lateral and medial compartments that are similar to the two extrema observed on the measured potential distributions shown in FIGS. 6, 7 and 8. This computer model uses a simplified geometry to represent regions of different electrical conductivities inside the knee: bone (0.04 S/m), cartilage (0.18 S/m), muscle (0.35 S/m), fat (0.04 S/m); the potential distribution is computed using the finite element approach (Comsol™ software); the electrical sources are two rims of uniform impressed current density located at the periphery of the two regions of compressed cartilage.

Figure 10B:
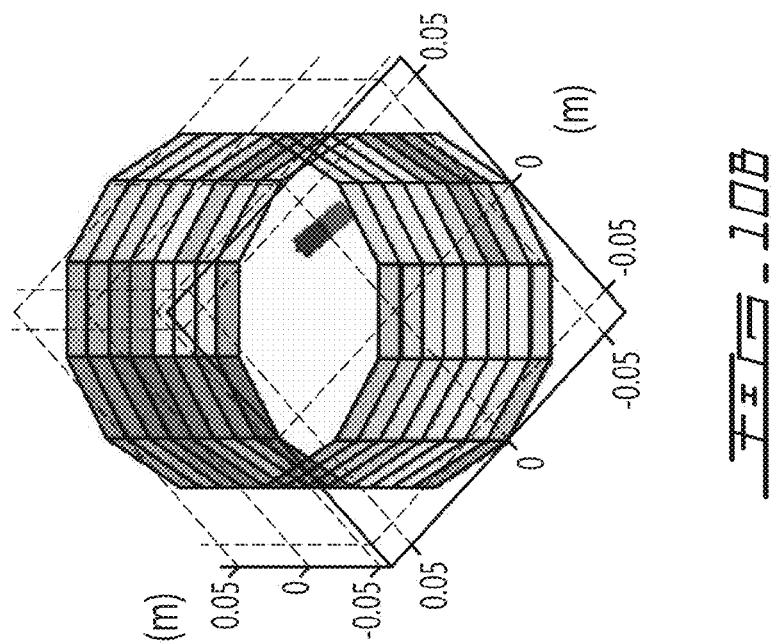
FIGS. 10A and B illustrate the position and orientation of a current dipole that generates potentials on the surface of a cylindrical volume conductor that reproduce the recorded knee surface potentials for a particular case, wherein at this instant of time, the potential distribution is mostly dipolar and the current dipole is located at the articular surface of the lateral compartment, the distance scale being expressed in meters, in accordance with an embodiment.
Figure 10A:
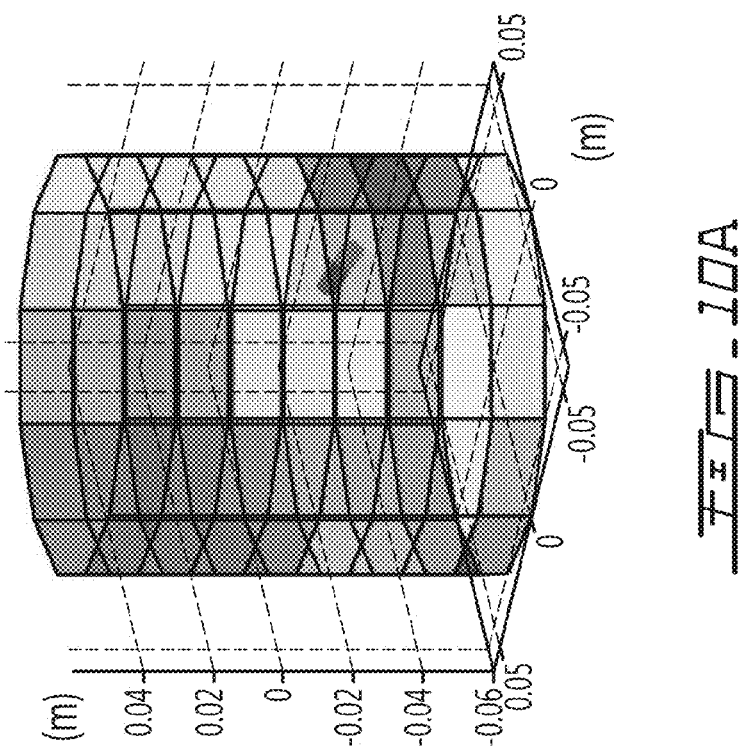

Additional means of source localization and characterization are also possible, such as those shown in FIG. 10. There is illustrated the position and orientation of a current dipole that generated potentials for a particular case. The potentials were modeled to occur at the sites of the recording electrodes over a cylindrical volume conductor with a similar geometry to that of the knee, i.e. a diameter of 10 cm, using the formula:

$$\phi = p \cdot (r-r')/(4\pi\sigma|r-r'|^3)$$

where $\phi$ is the computed potential (V), p is the dipole moment (A-m), r is the position of an electrode, r' is the position of the dipole, $\sigma$ is the electrical conductivity (S/m). The position r' and moment p of the dipole that minimize the sum of the squares of the differences between the measured and computed potential at all the electrode sites are computed using the Nelder-Mead simplex (direct search) method. The computed dipole is shown in FIG. 10 over the lateral compartment. At this point in time, the potential distribution is mostly dipolar with a single antero-lateral maximum and the dipole is approximately at the articular surface of the lateral compartment. Here again the position and orientation of the dipole are consistent with the generation by streaming potentials in articular cartilage since the dipole's positive end points out of the articulating surface due to excess sodium ions being driven out of the cartilage by load induced convection of interstitial fluid.

It should be noted that articular cartilage bears a net negative charge fixed to its extracellular matrix due to its high proteoglycan content that induces an excess of sodium versus chloride in the interstitial fluid as described by the Donnan equilibrium. Thus compressing cartilage generates fluid convection of this excess sodium relative to the negative charge fixed to the extracellular matrix of cartilage.

Additionally, goniometers, accelerometers or sensors can be placed near the joint to measure the angle of the joint and/or measuring forces exerted by the subject during loading.

The clinical interpretation of the electroarthrogram to determine joint health versus disease or normal versus abnormal cartilage and meniscus function, can be based on variables derived from the maps such as the amplitude, position and timing of the potential extrema, the surface integral values, or the time integral values of the signals, and of other variables obtained with volume conductor and source modeling. These EAG variables should be interpreted in conjunction with other physical variables such as the acceleration of the articulation and the mass of the subject, and other clinical variables such as the age, sex and clinical history of the patient.

Figure 12:
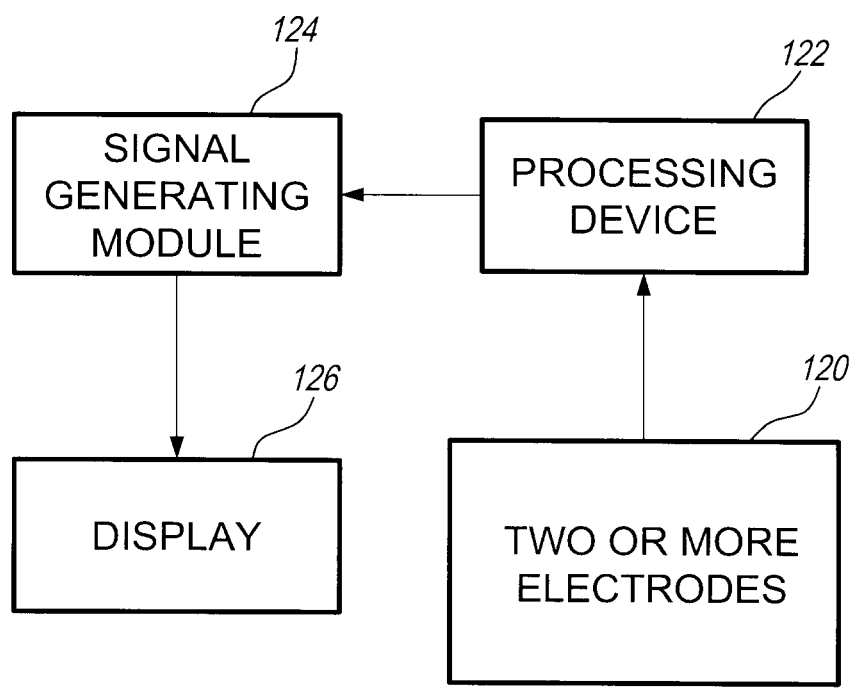
FIG. 12 is a block diagram of an embodiment of a system for non-invasively measuring electrical activity in a joint of a subject.

FIG. 12 illustrates a system for non-invasively measuring an electrical activity in a joint of a subject. At least two electrodes 120 are provided on the surface of the skin, directly or indirectly, such that they may capture electroarthrographic potentials that are generated within the joint when the articulation is loaded. The electroarthrographic potentials are then transmitted to a processing device 122. Processing involves discriminating between electroarthrographic potentials originating from the loading of joint tissues in the articulation and those from other sources. Once the appropriate electroarthrographic potentials have been isolated, they are transmitted to a signal generating module 124 which will generate the signals that represent articular cartilage, and other joint tissue such as meniscus, activity. Multiple formats can be used to display and/or to quantify the signals that represent joint tissue activity such as: an isopotential map at a specific time instant (FIG. 5); sequences of isopotential maps during the loading process (FIGS. 6 to 8); the magnitude and position of potential extrema at a specific time instant; the magnitude of potential extrema for one specific electrode site during the loading process; surface integrals of an isopotential map or of segments of an isopotential map at a specific time instant; time integrals of a series of isopotential maps, and; equivalent representations of the bioelectrical EAG sources. These equivalent representations are computed so as to best reproduce the measured potential distribution over the surface of a volume conductor model of the articulation and can be, but are not limited to: a single current dipole (FIG. 10); multiple current dipoles (2, 3, 4, 5, 6, 7, 8, 9, 10, and more than 10); the potential distributions over the closed surfaces that surround the compressed cartilage; the current density distributions over the closed surfaces that surround the compressed cartilage; and the current density distributions inside the compressed cartilage.

In one embodiment, the system also comprises a loading device for applying a load to the articulation and thereby generate the electroarthrographic potentials in the joint. Systems which do not include a loading device are those where the loading is done in a manual fashion. The loading device can be electromechanical, piezoelectric, mechanical, or any other alternative that will cause the electric activity in the joint. In one embodiment, a goniometer, accelerometer and/or sensor are provided to measure at least one of an angle of the joint and measuring forces exerted by the subject during loading.

In some embodiments, the processing device 122 and signal generating module 124 as illustrated in FIG. 12 may be a general purpose computer equipped with software that allows it to receive data and process it accordingly to generate signals representing articular cartilage electrical activity. The results may be displayed in their present form on a screen or monitor 126 to be visualized by a user or operator. The information may also be used in conjunction with other known processing techniques to assist in diagnostics of joint injury and disease. The diagnostic information can be obtained from the signals representing articular cartilage and other joint tissue electrical activity as a function of the force applied to the articulation, and also as a function of the angle of the articulation. As examples, reduced electrical activity from cartilage may represent increasing joint degeneration and osteoarthritis or a local injury of cartilage. Meniscus degeneration or injury will also result in reduced electrical activity since meniscus can be a source of streaming potentials. Meniscus injury will be reflected in the distribution and magnitude of electrical fields since loading of both articular cartilage and meniscus is greatly dependent on the state of the meniscus.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

While illustrated in the block diagrams as groups of discrete components communicating with each other via distinct data signal connections, it will be understood by those skilled in the art that the preferred embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present embodiments. The embodiments of the invention described above are intended to be exemplary only. The scope of the invention is therefore intended to be limited solely by the scope of the appended claims.

What is claimed is:

1. A method for non-invasively measuring electrical activity in a live joint of a subject, the method comprising:
removably attaching in a non-invasive manner at least two electrodes to a skin surface around an articulation comprising the live joint;
generating electroarthrographic potentials within the live joint by loading the articulation;
capturing said electroarthrographic potentials using said at least two electrodes;
discriminating between electroarthrographic potentials originating from joint tissue activity and electrical potentials generated by other sources within the subject; and
generating measurement signals representing the electrical activity of joint tissue.

2. The method of claim 1, wherein said generating electroarthrographic potentials comprises one of loading the articulation manually, loading the articulation with an electromechanical loading device, and loading the articulation with a piezoelectric loading device.

3. The method of claim 1, further comprising displaying said signals generated in the form of an electroarthrogram.

4. The method of claim 1, further comprising placing at least one of goniometers, accelerometers and sensors adjacent to the live joint to measure at least one of an angle of the live joint and forces exerted by the subject during loading.

5. The method of claim 1, wherein said discriminating between electroarthrographic potentials originating from joint tissue activity and electrical potentials generated by other sources within the subject comprises subtracting at each instant in time a weighted average of electrical potentials originating from the electrodes so as to measure the electroarthrographic potentials with respect to an absolute reference.

6. The method of claim 1, wherein said discriminating between electroarthrographic potentials originating from joint tissue activity and electrical potentials generated by other sources within the subject comprises band pass filtering.

7. The method of claim 1, wherein said discriminating between electroarthrographic potentials originating from joint tissue activity and electrical potentials generated by other sources within the subject comprises low pass filtering.

8. The method of claim 1, wherein discriminating between electroarthrographic potentials originating from joint tissue activity and electrical potentials generated by other sources within the subject comprises high pass filtering.

9. The method of claim 1, further comprising displaying said signals generated in the form of sequences, movies, isopotential maps or 3D potential surfaces.

10. The method of claim 1, further comprising calculating electrical sources within the live joint and representing said electrical sources as electric fields, currents, polarization or charges.

11. The method of claim 1, wherein said discriminating comprises discriminating between electrical potentials originating from cartilage and electrical potentials generated by other sources within the subject.

12. The method of claim 1, wherein said removably attaching in a non-invasive manner at least two electrodes comprises selecting at least two electrodes from the group consisting of electroencephalographic electrodes, self-adhesive electrocardiographic electrodes and electrodes embedded in a cuff or a sleeve adapted to fit around the live joint.

13. The method of claim 1, wherein said removably attaching comprises evenly placing the electrodes in contact with the skin surface around the live joint.

14. The method of claim 1, wherein said removably attaching comprises attaching a reference electrode and a drive electrode to inject current so as to minimize electrical interference.

15. The method of claim 1, wherein said removably attaching comprises attaching electrodes having low noise.

16. The method of claim 1, wherein said removably attaching comprises attaching electrodes made of Ag—AgCl.

17. The method of claim 1, further comprising determining from the measurement signals at least one of a function of joint tissues, degradation of joint tissues, osteoarthritis or arthritis in a patient.

18. A system for non-invasively measuring an electrical activity in a live joint of a subject, the system comprising:
- at least two spaced apart electrodes for contacting the skin around an articulation comprising the live joint and capturing electroarthrographic potentials generated within the live joint by loading the articulation;
- a processing device adapted to receive the electroarthrogaphic potentials from the at least two electrodes and to discriminate between electroarthrographic potentials originating from joint tissue activity and electrical potentials generated by other sources within the subject; and
- a signal generating module adapted to receive the electroarthrographic potentials originating from joint tissue activity and generate measurement signals representing the joint tissue activity.

19. The system of claim 18, further comprising a loading device for applying a load to the articulation and thereby generating the electroarthrographic potentials in the live joint.

20. The system of claim 19, wherein the loading device is one of electromechanical and piezoelectric.

21. The system of claim 18, further comprising placing at least one of a goniometer, accelerometers and sensor to measure at least one of an angle of the live joint and forces exerted by the subject during loading.

22. The system of claim 18, wherein said at least two electrodes are selected from the group consisting of electroencephalographic electrodes, self-adhesive electrocardiographic electrodes and electrodes embedded in a cuff or a sleeve adapted to fit around the live joint.

23. The system of claim 18, wherein the electrodes are made of Ag—AgCl.

24. The system of claim 18, wherein the processing device is adapted to discriminate between electroarthrographic potentials originating from cartilage activity and electrical potentials generated by other sources within the subject.

25. The system of claim 18, wherein the processing device is further adapted to determine from the measurement signals at least one of a function of joint tissues, degradation of joint tissues, osteoarthritis or arthritis in a patient.

* * * * *